United States Patent
Peters et al.

(10) Patent No.: US 9,173,551 B2
(45) Date of Patent: Nov. 3, 2015

(54) ENHANCED CONTROL OF FLEXIBLE ENDOSCOPES THROUGH HUMAN-MACHINE INTERFACE

(75) Inventors: Craig Peters, McLean, VA (US); Kevin Cleary, Potomac, MD (US); Haifeng Luo, Beijing (CN)

(73) Assignee: Children's National Medical Center, Washington, DC (US)

( * ) Notice: Subject to any disclaimer, the term of this patent is extended or adjusted under 35 U.S.C. 154(b) by 188 days.

(21) Appl. No.: 13/608,487

(22) Filed: Sep. 10, 2012

(65) Prior Publication Data

US 2013/0123580 A1 May 16, 2013

Related U.S. Application Data

(60) Provisional application No. 61/532,916, filed on Sep. 9, 2011.

(51) Int. Cl.
*A61B 1/00* (2006.01)
*A61B 1/005* (2006.01)
*A61B 1/307* (2006.01)

(52) U.S. Cl.
CPC .......... *A61B 1/0057* (2013.01); *A61B 1/00006* (2013.01); *A61B 1/307* (2013.01)

(58) Field of Classification Search
CPC .. A61B 1/00006; A61B 1/0057; A61B 1/307; A61B 2019/2211; A61B 2019/2276; A61B 17/3417; A61B 17/3421; A61B 19/201; A61B 19/22; A61B 19/2203; A61B 1/00147; A61B 1/0051; A61B 2017/003; A61B 2019/2242; A61M 25/0105; A61M 25/0133
USPC ......... 600/104, 102, 424, 114, 118, 149, 427; 604/95.04
See application file for complete search history.

(56) References Cited

U.S. PATENT DOCUMENTS

| | | | |
|---|---|---|---|
| 4,802,487 A * | 2/1989 | Martin et al. ................ 600/463 |
| 6,096,004 A * | 8/2000 | Meglan et al. ............ 604/95.01 |
| 6,292,681 B1 * | 9/2001 | Moore .......................... 600/407 |
| 7,090,683 B2 * | 8/2006 | Brock et al. .................. 606/130 |
| 7,811,294 B2 * | 10/2010 | Strommer et al. ............ 606/108 |
| 7,887,549 B2 * | 2/2011 | Wenderow et al. ........... 606/108 |
| 7,901,348 B2 * | 3/2011 | Soper et al. ................... 600/117 |
| 8,257,302 B2 * | 9/2012 | Beyar et al. ................ 604/95.01 |
| 2002/0143319 A1 * | 10/2002 | Brock ............................... 606/1 |
| 2003/0195389 A1 | 10/2003 | Motoki et al. |
| 2005/0272976 A1 | 12/2005 | Tanaka et al. |

(Continued)

OTHER PUBLICATIONS

Matlaga, B. and J. Lingeman (2012). Surgical Management of Upper Urinary Tract Calculi. Campbell-Walsh Textbook of Urology. A. Wein, L. Kavoussi, A. Novick, A.Partin and C. Peters. Philadelphia, Elsevier, Inc. 2: 1357-1410.

(Continued)

*Primary Examiner* — John P Leubecker
*Assistant Examiner* — Arnaldo Torres Diaz
(74) *Attorney, Agent, or Firm* — Oblon, McClelland, Maier & Neustadt, L.L.P.

(57) ABSTRACT

An electromechanical drive system with drop-in capability allows manipulation of the majority of existing endoscopes. The invention does not require retrofitting of existing endoscopes and maintains the current clinical workflow. The drive system can be controlled through a human/machine interface, which could consist of a variety of different input devices, including a joystick, keyboard, or game controller.

31 Claims, 6 Drawing Sheets

(56) References Cited

U.S. PATENT DOCUMENTS

| | | |
|---|---|---|
| 2007/0185485 A1* | 8/2007 | Hauck et al. .................. 606/41 |
| 2007/0185486 A1* | 8/2007 | Hauck et al. .................. 606/41 |
| 2007/0198008 A1* | 8/2007 | Hauck et al. .................. 606/41 |
| 2008/0009791 A1* | 1/2008 | Cohen et al. ............... 604/95.01 |
| 2008/0045794 A1 | 2/2008 | Belson |
| 2009/0105639 A1* | 4/2009 | Weitzner et al. ........... 604/95.01 |
| 2009/0247944 A1* | 10/2009 | Kirschenman et al. .... 604/95.04 |
| 2009/0247993 A1* | 10/2009 | Kirschenman et al. .......... 606/1 |
| 2010/0022825 A1 | 1/2010 | Yoshie |
| 2010/0069833 A1* | 3/2010 | Wenderow et al. ........ 604/95.01 |
| 2010/0076310 A1* | 3/2010 | Wenderow et al. ........... 600/434 |
| 2010/0274079 A1 | 10/2010 | Kim et al. |
| 2011/0213384 A1 | 9/2011 | Jeong |
| 2012/0289783 A1* | 11/2012 | Duindam et al. ............. 600/118 |

OTHER PUBLICATIONS

Sagalowsky, A., T. Jarrett, et al. (2012). Urothelial Tumors of the Upper Urinary Tract and Ureter. Campbell-Walsh Textbook of Urology. A. Wein, L. Kavoussi, A. Novick, A. Partin and C. Peters. Philadelphia, Elsevier, Inc. 2: 1516-1553.

Berguer R., M. Remler and D. Beckley, Laparoscopic instruments cause increased forearm fatigue: A subjective and objective comparison of open and laparoscopic techniques, 1997, vol. 6, No. 1, pp. 36-40.

Desai, M. M., M Aron, I. S. Gill, G Pascal-Haber, O Ukimura, J. H. Kaouk, G Stahler, F Barbagil, C Carlson, F Moll, "Flexible robotic retrograde renoscopy: Description of novel robotic device and preliminary laboratory experience", Urology 2008; 72: 42-46.

Fernández-Esparrach, G., R. S. J. Estépar, C Guarner-Argente, G Martinez-Pallí, R Navarro, C. R. de Miguel, H Córdova, C. C. Thompson, A. M. Lacy, L Donoso, J. R. Ayuso-Colella, A Ginès, M Pellisé, J Llach, K. G. Vosburgh, "The role of a computed tomography-based image registered navigation system for natural orifice transluminal endoscopic surgery: a comparative study in a porcine model", Endoscopy 2010; 42(12): 1096-1103.

Harewood, G.C., KristiaChrysostomou, NailaHimy and Wai Ling Leong, Impact of Operator Fatigue on Endoscopy Performance: Implications for Procedure Scheduling, Digestive Diseases and Sciences 2009, vol. 54, No. 8, 1656-166.

Kerbl, K., Rehman, J., Landman, J. et al., Current management of urolithiasis: progress or regress? J. Endourology 16:281-8, 2002.

Rassweiler, J., M Baumhauer, U Weickert, H-P Meinzer, D Teber, L-M Su, V. R. Patel, "The Role of Imaging and Navigation for Natural Orifice Translumenal Endoscopic Surgery", J. Endourology 2009; 23(5): 793-802.

Schuster, TG, Hollenbeck, BK, Faerber, GJ, Wolf, JS, Jr., Complications of ureteroscopy: analysis of predictive factors. J Urol 166:538-40, 2001.

Abu Ghazaleh, L. A., A. N. Shunaigat, et al. (2011). "Retrograde intrarenal lithotripsy for small renal stones in prepubertal children." Saudi journal of kidney diseases and transplantation : an official publication of the Saudi Center for Organ Transplantation, Saudi Arabia 22(3): 492-496.

Cannon, G. M., M. C. Smaldone, et al. (2007). "Ureteroscopic management of lower-pole stones in a pediatric population." Journal of endourology / Endourological Society 21(10): 1179-1182.

Duty, B., Z. Okhunov, et al. (2012). "Medical malpractice in endourology: analysis of closed cases from the State of New York." The Journal of urology 187(2): 528-532.

Hellawell, G. O., S. J. Mutch, et al. (2005). "Radiation exposure and the urologist: what are the risks?" The Journal of urology 174(3): 948-952; discussion 952.

Hristova-Popova, J., I. Saltirov, et al. (2011). "Exposure to patient during interventional endourological procedures." Radiation protection dosimetry 147(1-2):114-117.

Kim, S. S., T. F. Kolon, et al. (2008). "Pediatric flexible ureteroscopic lithotripsy: the children's hospital of Philadelphia experience." The Journal of urology 180(6): 2616-2619; discussion 2619.

Kokorowski, P. J., J. S. Chow, et al. (2012). "Prospective measurement of patient exposure to radiation during pediatric ureteroscopy." The Journal of urology 187(4): 1408-1414.

Landman, J., D. I. Lee, et al. (2003). "Evaluation of overall costs of currently available small flexible ureteroscopes." Urology 62(2): 218-222.

Nerli, R. B., S. M. Patil, et al. (2011). "Flexible ureteroscopy for upper ureteral calculi in children." Journal of endourology / Endourological Society 25(4):579-582.

Osman, N. I. and G. N. Collins (2011). "Urological litigation in the UK National Health Service (NHS): an analysis of 14 years of successful claims." BJU international 108(2): 162-165.

Pietrow, P. K., B. K. Auge, et al. (2002). "Techniques to maximize flexible ureteroscope longevity." Urology 60(5): 784-788.

Reddy, P. P. and W. R. Defoor (2010). "Ureteroscopy: The standard of care in the management of upper tract urolithiasis in children." Indian journal of urology: IJU ; journal of the Urological Society of India 26(4): 555-563.

Smaldone, M. C., G. M. Cannon, Jr., et al. (2007). "Is ureteroscopy first line treatment for pediatric stone disease?" The Journal of urology 178(5): 2128-2131; discussion 2131.

Sobel, D. L., K. R. Loughlin, et al. (2006). "Medical malpractice liability in clinical urology: a survey of practicing urologists." The Journal of urology 175(5): 1847-1851.

Sung, J. C., W. P. Springhart, et al. (2005). "Location and etiology of flexible and semirigid ureteroscope damage." Urology 66(5): 958-963.

Taie, K., M. Jasemi, et al. (2012). "Prevalence and management of complications of ureteroscopy: a seven-year experience with introduction of a new maneuver to prevent ureteral avulsion." Urology journal 9(1): 356-360.

Tanaka, S. T., J. H. Makari, et al. (2008). "Pediatric ureteroscopic management of intrarenal calculi." The Journal of urology 180(5): 2150-2153; discussion 2153-2154.

Thomas, J. C. (2010). "How effective is ureteroscopy in the treatment of pediatric stone disease?" Urological research 38(4): 333-335.

Unsal, A. and B. Resorlu (2011). "Retrograde intrarenal surgery in infants and preschool-age children." Journal of pediatric surgery 46(11): 2195-2199.

Wang, H. H., L. Huang, et al. (2011). "Use of the ureteral access sheath during ureteroscopy in children." The Journal of urology 186(4 Suppl): 1728-1733.

Wang, H. H., L. Huang, et al. (2012). "Shock wave lithotripsy vs ureteroscopy: variation in surgical management of kidney stones at freestanding children's hospitals." The Journal of urology 187(4): 1402-1407.

* cited by examiner

ENHANCED CONTROL OF FLEXIBLE ENDOSCOPES THROUGH HUMAN-MACHINE INTERFACE

REFERENCE TO RELATED APPLICATION

The present application claims the benefit of U.S. Provisional Patent Application No. 61/532,916, filed Sep. 9, 2011, whose disclosure is hereby incorporated by reference in its entirety into the present disclosure.

FIELD OF THE INVENTION

The invention concerns the development of an integrated control/movement system and human/machine interface to enhance flexible endoscopy. The initial application considered is ureteroscopy but the invention is applicable to numerous endoscopic procedures, including but not limited to colonoscopy, gastroscopy, duodenoscopy, bronchoscopy, ventriculoscopy, and sinus endoscopy.

BACKGROUND OF THE INVENTION

Flexible endoscopy is a ubiquitous means of diagnosis and therapy in nearly all aspects of medicine, including ureteroscopy, colonoscopy, gastroscopy, duodenoscopy, bronchoscopy, ventriculoscopy, and sinus endoscopy. Endoscopic systems from the major manufacturers are very similar with controls based on simple flexion of the tip of the endoscope, rotational control, and in and out translational movement. These three movements are controlled by the operator at the head of the instrument and are all distinct in their character, making intuitive control difficult to learn and perform. Efficient and safe control could be enhanced by a control interface that permits intuitive movements with faithful visual feedback (e.g. when a target is identified, it can be reached smoothly). Because of the complexity of movements needed for many applications, an integrated movement/control system would have the potential to greatly enhance the safety, efficacy, and efficiency of these instruments. While physicians who do endoscopy every day become quite skilled at the contortions that can be needed for effective placement of the instrument tip, the shortcomings of the current approach extend the time required for procedures [Harewood 2008], increase user fatigue [Berguer 2007], and have the potential to increase the frequency of errors. For those physicians who perform endoscopy on an occasional basis, the need for a more user-friendly, intuitive means of control becomes even more pronounced.

The basic design and functionality of all flexible endoscopes is similar, with differences dependent upon size. Smaller instruments have simpler but more limited control mechanisms with fewer degrees of freedom. Uretero-renoscopy is often performed with flexible ureteroscopes for access and manipulation in the ureter and kidney. Uses include stone removal, diagnosis for bleeding or malignancy, as well as direct biopsy and destruction of malignant lesions. In stone disease, ureteroscopy is becoming more widely used than the other minimally invasive means to remove stones in both adults and children [Kerbl 2002]. Ureteroscopes have improved in visual acuity and have become small enough to minimize trauma and permit use in small children. They have greater flexion capacity but remain controlled by the basic three-function mechanisms. Control is performed with two hands, one to move the ureteroscope in and out, and the other to rotate and flex the ureteroscope. This leaves no hand free to perform manipulations through the working port, which can include stone basketing, laser lithotripsy, tumor fulguration, or biopsy. In many clinical situations, the entire interior of the kidney must be carefully inspected to avoid leaving stone fragments or residual tumor. This requires moving the ureteroscope into each of the 10 to 12 calyces in the human kidney. Such delicate control requires significant skill and is often challenging and slow, even for the experienced endoscopist, particularly in the lower pole of the kidney where the instrument must be tightly flexed and then rotated and pulled back to move into the lower calyces.

Manipulation of the endoscope can be challenging, even for experienced physicians. The physician is typically watching the video image from the endoscope, while trying to navigate the anatomy. The physician must make the mental map from the anatomy to control the endoscope, which is often complex. Development of an effective and intuitive control system based on the visual image and directionality of the endoscope would be of great value in enhancing safety, efficiency, and efficacy of these procedures. It is well documented that more complex procedures require more time endoscopically and may have to be staged due to time constraints [Schuster 2001]. Particularly with regard to ureteroscopy, minimizing the time of the procedure is important since injury to the interior of the kidney may occur with ongoing ureteroscope manipulation and infusion of irrigating fluid to provide a clear view. With the complex movements needed to direct the ureteroscope tip to a particular location, the orientation of the visual field changes, which disorients the operator and renders the combination of movements needed to achieve the required direction not intuitively apparent. The complex choreography of movements needed to direct the ureteroscope into the various parts of the kidney is neither ergonomic nor efficient.

The importance of positional information through navigation has been recognized for many years, but there remains no clinically effective system for instrument navigation in the abdomen or urinary tract. This importance has been described with reference to the needs of natural orifice transluminal endoscopic surgery (NOTES) [Rasswiler et al. 2009]. Endoscopic procedures necessarily imply limitations in perception and spatial orientation of tools. Left unresolved, these limitations give rise to surgical complications. Fernández-Esparrach et al. conducted animal studies to assess the role of CT-based navigation for NOTES. This study resulted in minor complications in 40% of standard approach procedures, compared with 13% in procedures employing navigation through preoperative CT-based image registration [Fernández-Esparrach et al. 2010].

Several groups have investigated navigation in flexible endoscopy, but there is currently no commercially available system that integrates a robotic-like control system with flexible endoscopy. The Hansen Medical robotic catheter system (Sensei, Hansen Medical, Mountainview, Calif.) is most similar in concept, but drives a passive catheter element and relies solely on visual feedback. Initially developed for intracardiac electrophysiologic applications, a modified system was used to perform flexible uretero-renoscopy in swine [Desai et al. 2008]. This modified system was recently extended to humans in an 18 patient study of laser lithotripsy for renal calculi [Desai et al. 2011]. This system, while similar in principle, uses a steerable guide catheter and sheath assembly to control catheter placement. Limitations with such an approach include lack of intuitive control and positional information. In summary, we are not aware of any system that provides the capabilities of precision device manipulation proposed here by providing a "snap-in capability" for existing endoscopes as described below.

REFERENCES FOR THIS SECTION

Berguer R., M. Remler and D. Beckley, Laparoscopic instruments cause increased forearm fatigue: A subjective and objective comparison of open and laparoscopic techniques, 1997, Vol. 6, No. 1, Pages 36-40

Desai, M. M., M Aron, I. S. Gill, G Pascal-Haber, O Ukimura, J. H. Kaouk, G Stahler, F Barbagil, C Carison, F Moll, "Flexible robotic retrograde renoscopy: Description of novel robotic device and preliminary laboratory experience", Urology 2008; 72: 42-46.

Fernández-Esparrach, G., R. S. J. Estépar, C Guarner-Argente, G Martínez-Pallí, R Navarro, C. R. de Miguel, H Córdova, C. C. Thompson, A. M. Lacy, L Donoso, J. R. Ayuso-Colella, A Ginès, M Pellisé, J Llach, K. G. Vosburgh, "The role of a computed tomography-based image registered navigation system for natural orifice transluminal endoscopic surgery: a comparative study in a porcine model", Endoscopy 2010; 42(12): 1096-1103.

Harewood, G. C., KristiaChrysostomou, NailaHimy and Wai Ling Leong, Impact of Operator Fatigue on Endoscopy Performance: Implications for Procedure Scheduling, Digestive Diseases and Sciences 2009, Volume 54, Number 8, 1656-166.

Kerbl, K., Rehman, J., Landman, J. et al., Current management of urolithiasis: progress or regress? J. Endourology 16:281-8, 2002

Rassweiler, J., M Baumhauer, U Weickert, H-P Meinzer, D Teber, L-M Su, V. R. Patel, "The Role of Imaging and Navigation for Natural Orifice Translumenal Endoscopic Surgery", J. Endourology 2009; 23(5): 793-802.

Schuster, T G, Hollenbeck, B K, Faerber, G J, Wolf, J S, Jr., Complications of ureteroscopy: analysis of predictive factors. J Urol 166:538-40, 2001

OBJECTS AND SUMMARY OF THE INVENTION

Accordingly, one object of one or more aspects of the invention is an electromechanical system to provide "power steering" of the endoscope for more precise and stable control than can be achieved by the current method of using a human operator.

Another objective of the method is to provide a mechanical device to stably hold the endoscope, along with a mechanism for precise actuation of translation, rotation, and tip flexion.

A related objective is to provide an electromechanical system that can be interfaced to a variety of input devices through a human machine interface.

A further objective of the method is to provide a general solution that is applicable to the majority of current flexible endoscopes without the need to retrofit the endoscope itself.

Yet another objective of the present invention is to provide a movement control device that will fit conventional flexible endoscopes and permit enhanced control of the endoscope through a natural user interface that translates operator movements that are visually guided to endoscope motion.

These and additional objects are accomplished by the various aspects of the present invention, where an existing flexible endoscope can be placed in a mechanical platform with capabilities for actuation of translation, rotation, and tip flexion; the mechanical platform can be controlled by a microprocessor-based commercially available motion control card; and the system can be interfaced to a variety of user input devices including joysticks, 6 degree of freedom mice such as the SpaceNavigator or any conventional mouse, and other input devices, including a keyboard.

Aspects of the invention in at least some embodiments include:

By providing a user interface for the control of a flexible endoscope, this system aims to enhance flexible endoscopic control, targeting, precision and safety.

Its design as a separate component that can be added to any flexible endoscope permits this level of enhanced control without requiring the creation and purchase of a new or different flexible endoscope.

The ability to integrate with any flexible endoscope permits application in a wide variety of ages, including the small endoscopes used in pediatric applications.

The familiar user interface (e.g., joystick, mouse, keyboard, other input device, or combination thereof) permits more natural control as well as facilitating the operator's manipulation of any working instruments that are passed through the endoscope for actual manipulation of the tissue being examined, thereby enhancing the operative efficacy of the endoscope.

The control system will permit integration with navigational and mapping functions to enhance accuracy and targeting efficiency and efficacy.

The enhancements that the present invention in at least some embodiments provides over conventional flexible endoscopy are:

More natural user interface for endoscopic control.

Enhanced efficiency of operation for the widest user range, particularly the non-expert.

Enhanced safety profile due to more accurate movement.

Reduced instrument damage due to more controlled application, thereby reducing costs.

Reduced radiation exposure to patient and operator due to enhanced control.

The scope of use includes, but is not limited to, the following:

Urology—flexible ureteroscopy for renal stones, tumor, bleeding, surveillance for tumor, diagnosis for bleeding.

Pulmonary—flexible bronchoscopy for diagnosis and therapy of various conditions.

Gastroenterology—upper GI endoscopy of stomach, duodenum, cholangiography, ERCP, small bowel diagnosis; lower GI endoscopy for colonoscopy for diagnosis and treatment of tumor, polyp, screening for various lower GI conditions.

Otolaryngology—sinus surgery using flexible endoscopy.

Neurosurgery—ventriculoscopy for hydrocephalus and diagnosis.

All of these procedures have been widely undertaken with conventional flexible endoscopes of differing sizes. The control systems are identical and require the same complex manipulation for adequate control. Enhancements that could potentially use conventional endoscopes have the potential to be useful for a variety of procedures.

The advantages offered by of the present invention include, but are not limited to, the following:

Operative Accuracy and Efficiency

Ureteroscopic efficacy is dependent upon the procedure being performed, the most common being stone extraction. Success in stone cases is heavily determined by stone location, with lower pole stones being the most challenging, and by stone size. Published stone-free rates in adults range from 31 to 90+%, with lower pole stone-free rates being between 31 and 87%. Residual stone fragments are at high risk for re-growth and continued clinical morbidity. This necessitates further interventions with risks and morbidity. (Matlaga and Lingeman 2012)

Pediatric stone free rates are less available due to lower incidence, but range from 50 to 87% at first treatment. Again, size and location are critical determinants. (Cannon, Smaldone et al. 2007; Smaldone, Cannon et al. 2007; Kim, Kolon et al. 2008; Tanaka, Makari et al. 2008; Reddy and Defoor 2010; Thomas 2010; Abu Ghazaleh, Shunaigat et al. 2011; Nerli, Patil et al. 2011; Unsal and Resorlu 2011; Wang, Huang et al. 2012)

Factors contributing to lack of success include inability to access the stone due to position, as well as the inability to find the stone due to inadequate navigational control. Once the stone is accessed, it must be fragmented, requiring delicate positioning of the laser fiber to the stone to maximize energy transfer without injuring renal tissue. There is a time limit to performing ureteroscopy due to the need for irrigation and possible extravasation of irrigant and injury to the kidney and surrounding tissues, as well as cooling (particularly in children). Success then becomes a product of the efficiency of identification, access, fragmentation, and fragment removal in a time-limited procedure. Efficiency and efficacy of action are therefore the critical determinants of success in any operator's hands.

Intra-renal stones have a lower success rate than ureteral stones. (Reddy and Defoor 2010) Lower pole stones have the lowest success rates of intra-renal stones, largely due to the difficulty of access. (Cannon, Smaldone et al. 2007; Matlaga and Lingeman 2012)

Tumor ablation is also a time-limited procedure for similar reasons. It is perhaps more challenging since tumor removal causes irrigant extravasation as the urothelium must be removed with the tumor. This need is further enhanced as the entire collecting system must be examined for other possible tumors, as the most common upper tract tumor amenable to ureteroscopic resection is transitional cell carcinoma, a tumor with a characteristic field effect and multi-focality. (Sagalowsky, Jarrett et al. 2012)

Following initial tumor resection, continued periodic surveillance of the collecting system is required on a scheduled basis or in response to a positive cytology or urinary tumor marker. Such surveillance may not have a time demand except to limit operative duration morbidity, but demands extremely high thoroughness to avoid missing a newly developed tumor. These can be highly invasive and aggressive malignancies with limited chemotherapeutic options.

Less frequent needs for ureteroscopy include upper urinary tract bleeding due to small vascular malformations. These lesions can be identified and laser fulgurated but identifying them within the collecting system in which there is no specific predilection for location can be difficult. Again, thorough inspection of the entire collecting system is a critical necessity.

Operative Safety—Preventing Injury to Patient

While surgical outcome is of obvious importance, safety is an even greater priority. Flexible ureteroscopy evolved as a safer and more versatile alternative to the original rigid and semi-rigid ureteroscopy. Even so, flexible ureteroscopy has risks including ureteral and renal perforation, hemorrhage, and stricture. Each is preventable and would be likely reduced as risks with a more precise and efficient endoscopic control system. (Reddy and Defoor 2010; Wang, Huang et al. 2011; Matlaga and Lingeman 2012; Taie, Jasemi et al. 2012)

The incidence of ureteral and renal perforation with flexible ureteroscopy is reported between 1 and 4% for all stone procedures. These can result from inaccurate use of working elements as well as the ureteroscope itself. Perforation can usually be managed with stent drainage, but requires cessation of the procedure, and may necessitate a second procedure. The injury due to perforation, as well as overly aggressive ureteroscope movements and longer duration procedures, can cause stricture formation. Stricture rates are reported between 0.5 to 4% and can have significant short and long-term morbidity, at times requiring ureteral replacement. (Matlaga and Lingeman 2012) For stone cases, extrusion of the stone or fragment can occur in about 2% of cases. The most dangerous complication is ureteral avulsion and is fortunately rare at less than 1%, but more likely in the smaller ureter of children. (Taie, Jasemi et al. 2012)

Some injuries are limited yet cause short term bleeding that reduces visualization, necessitating premature cessation of the procedure. Failure of the initial procedure can therefore be due to relatively minor injuries that obscure vision. It is difficult to estimate the incidence of these injuries, but may represent at least 50% of failed initial cases of stone extraction.

Concomitant with ureteroscopy injuries is the potential for legal liability for these injuries. Endourology has been reported to generate the most number of claims within urology, with stone cases being the most common. (Sobel, Loughlin et al. 2006; Duty, Okhunov et al. 2012) Duty reviewed the patterns of medical malpractice actions for endourology in New York State. Ureteral perforation was a recognized aspect of these cases. Of all endourology cases, 40% were closed with indemnity at nearly $500,000 average. In the UK, Osman reported that in 493 cases resulting in payment, the most commonly implicated procedure was ureteroscopy with stenting. (Osman and Collins 2011)

Reduced Radiation Intra-Operatively

Conventional use of flexible ureteroscopy requires fluoroscopic image control for positioning and often this includes multiple images to confirm location and to correlate scope position and the target (stone or a particular anatomic landmark).

Estimates of radiation exposure have been published in ureteroscopy. Wieder reported exposures of 50 mGy/min of fluoroscopy. Total doses of approximately 560 cGy $cm^2$ have been published. (Hristova-Popova, Saltirov et al. 2011)

Only one study in children has been published but showed very high levels of exposure. Kokorowski et al., reported high exposure with a median skin entrance dose of 42.7 mGy (as compared to one CT scan of 10 mGy), suggesting exposures equivalent to nearly 10 CT scans. (Kokorowski, Chow et al. 2012)

Reduction in fluoroscopic imaging would be accomplished by better control of the ureteroscope or ultimately by alternative navigation systems.

Radiation to the physician is important as well and has been reported to be in the range of 1.9 to 12 mGy depending upon body part for each procedure. The critical aspect is that this is an accumulative dose. (Hellawell, Mutch et al. 2005)

Reduced Damage to Endoscopes

Modern ureteroscopes are expensive to purchase and to repair. Damage to endoscopes is extremely expensive and reduces the ability of a clinical unit to be productive if instruments are not available. (Landman, Lee et al. 2003)

Average number of uses of a modern ureteroscope is reported to be between 3 and 14 times, or 3 to 13 hours.

An analysis of the types of damage includes over-deflection and damage by working tools placed inappropriately.

Sung et al reported that most damage was due to operator error and over-deflection. (Pietrow, Auge et al. 2002; Sung, Springhart et al. 2005)

Controlling the performance of the ureteroscope could potentially reduce damage and reduce costs while maintaining availability.

References for this section:

Abu Ghazaleh, L. A., A. N. Shunaigat, et al. (2011). "Retrograde intrarenal lithotripsy for small renal stones in prepubertal children." *Saudi journal of kidney diseases and transplantation: an official publication of the Saudi Center for Organ Transplantation*, Saudi Arabia22(3): 492-496.

Cannon, G. M., M. C. Smaldone, et al. (2007). "Ureteroscopic management of lower-pole stones in a pediatric population." *Journal of endourology/Endourological Society*21 (10): 1179-1182.

Duty, B., Z. Okhunov, et al. (2012). "Medical malpractice in endourology: analysis of closed cases from the State of New York." *The Journal of urology*187(2): 528-532.

Hellawell, G. O., S. J. Mutch, et al. (2005). "Radiation exposure and the urologist: what are the risks?" *The Journal of urology*174(3): 948-952; discussion 952.

Hristova-Popova, J., I. Saltirov, et al. (2011). "Exposure to patient during interventional endourological procedures." *Radiation protection dosimetry*147(1-2): 114-117.

Kim, S. S., T. F. Kolon, et al. (2008). "Pediatric flexible ureteroscopic lithotripsy: the children's hospital of Philadelphia experience." *The Journal of urology*180(6): 2616-2619; discussion 2619.

Kokorowski, P. J., J. S. Chow, et al. (2012). "Prospective measurement of patient exposure to radiation during pediatric ureteroscopy." *The Journal of urology*187(4): 1408-1414.

Landman, J., D. I. Lee, et al. (2003). "Evaluation of overall costs of currently available small flexible ureteroscopes." *Urology*62(2): 218-222.

Matlaga, B. and J. Lingeman (2012). Surgical Management of Upper Urinary Tract Calculi. *Campbell-Walsh Textbook of Urology*. A. Wein, L. Kavoussi, A. Novick, A. Partin and C. Peters. Philadelphia, Elsevier, Inc. 2: 1357-1410.

Nerli, R. B., S. M. Patil, et al. (2011). "Flexible ureteroscopy for upper ureteral calculi in children." *Journal of endourology/Endourological Society*25(4): 579-582.

Osman, N. I. and G. N. Collins (2011). "Urological litigation in the UK National Health Service (NHS): an analysis of 14 years of successful claims." *BJU international*108(2): 162-165.

Pietrow, P. K., B. K. Auge, et al. (2002). "Techniques to maximize flexible ureteroscope longevity." *Urology*60(5): 784-788.

Reddy, P. P. and W. R. Defoor (2010). "Ureteroscopy: The standard of care in the management of upper tract urolithiasis in children." *Indian journal of urology: IJU: journal of the Urological Society of India*26(4): 555-563.

Sagalowsky, A., T. Jarrett, et al. (2012). Urothelial Tumors of the Upper Urinary Tract and Ureter. *Campbell-Walsh Textbook of Urology*. A. Wein, L. Kavoussi, A. Novick, A. Partin and C. Peters. Philadelphia, Elsevier, Inc. 2: 1516-1553.

Smaldone, M. C., G. M. Cannon, Jr., et al. (2007). "Is ureteroscopy first line treatment for pediatric stone disease?" *The Journal of urology*178(5): 2128-2131; discussion 2131.

Sobel, D. L., K. R. Loughlin, et al. (2006). "Medical malpractice liability in clinical urology: a survey of practicing urologists." *The Journal of urology*175(5): 1847-1851.

Sung, J. C., W. P. Springhart, et al. (2005). "Location and etiology of flexible and semirigid ureteroscope damage." *Urology*66(5): 958-963.

Taie, K., M. Jasemi, et al. (2012). "Prevalence and management of complications of ureteroscopy: a seven-year experience with introduction of a new maneuver to prevent ureteral avulsion." *Urology journal*9(1): 356-360.

Tanaka, S. T., J. H. Makari, et al. (2008). "Pediatric ureteroscopic management of intrarenal calculi." *The Journal of urology*180(5): 2150-2153; discussion 2153-2154.

Thomas, J. C. (2010). "How effective is ureteroscopy in the treatment of pediatric stone disease?" *Urological research*38 (4): 333-335.

Unsal, A. and B. Resorlu (2011). "Retrograde intrarenal surgery in infants and preschool-age children." *Journal of pediatric surgery*46(11): 2195-2199.

Wang, H. H., L. Huang, et al. (2011). "Use of the ureteral access sheath during ureteroscopy in children." *The Journal of urology*186(4 Suppl): 1728-1733.

Wang, H. H., L. Huang, et al. (2012). "Shock wave lithotripsy vs ureteroscopy: variation in surgical management of kidney stones at freestanding children's hospitals." *The Journal of urology*187(4): 1402-1407.

BRIEF DESCRIPTION OF THE DRAWINGS

A preferred embodiment of the present invention will be set forth in detail with reference to the drawings, in which.

DETAILED DESCRIPTION OF THE PREFERRED EMBODIMENT

A preferred embodiment and variations thereof will be set forth in detail with reference to the drawings, in which like elements refer to like elements or steps throughout.

Figure 1:
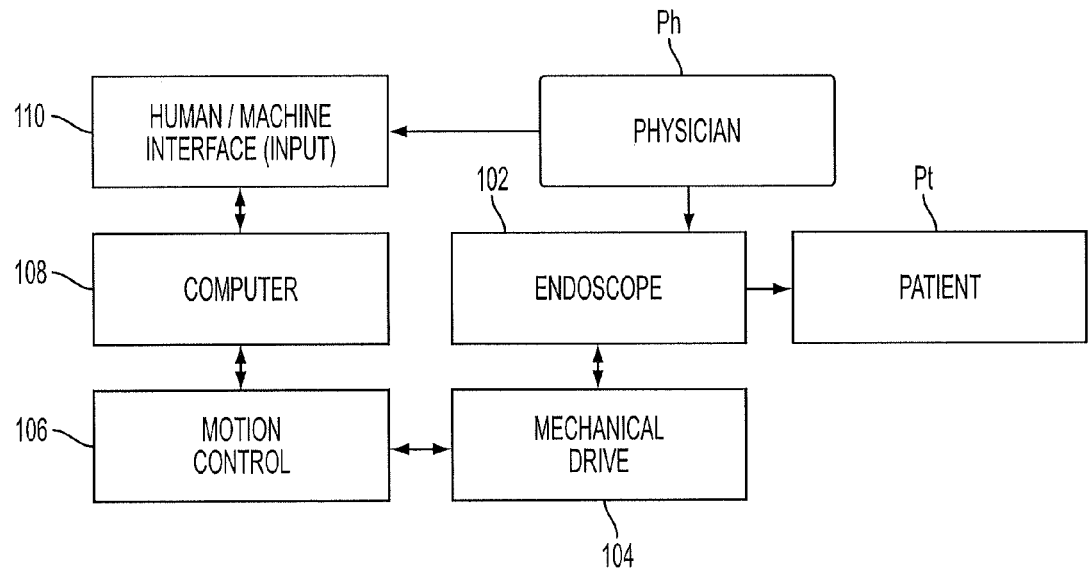
FIG. 1 is a block diagram of the overall system.

FIG. 1 illustrates the key features of the invention. The endoscope 102 is manipulated by the physician Ph to the region of interest within the patient Pt as done in current clinical practice. In the urinary tract, that would be up to the renal pelvis. The endoscope 102 is then placed in a mechanical drive system 104 that is capable of actuating translation, rotation, and tip flexion degrees of freedom. The mechanical drive system 104 is connected to a motion control system 106, which enables precision actuation of those degrees of freedom. The motion control system 106 connects to a personal computer 108 that connects to a human/machine interface (user input device) 110. The physician Ph then controls the endoscope 102 through the human/machine interface 110. The computer 108 accepts input commands from the human/machine interface 108 and translates the signals to the motion control system 106 to drive the motors on the mechanical drive system 104. The mechanical drive system 104 holds the endoscope 102 and mechanically actuates it so the tip can be precisely controlled within the patient body.

Figure 2:
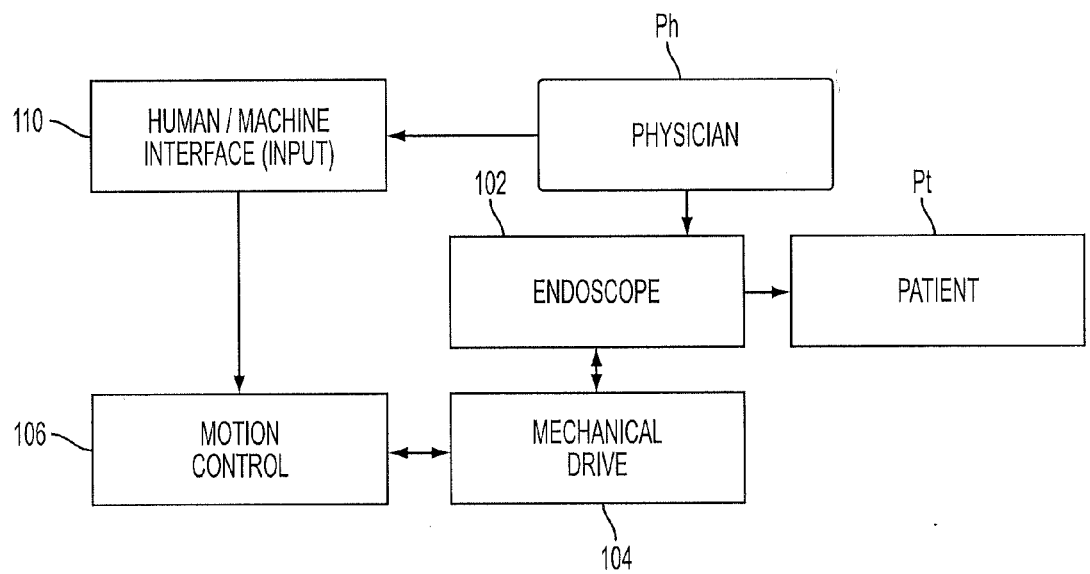
FIG. 2 is the same diagram showing that the system can be used without a control computer.

FIG. 2 is the same as FIG. 1 but shows that a control computer 108 is not necessary for this invention and instead that the human/machine interface 110 can be connected directly to the motion control system 106. The input devices can be selected based on physician preferences. Simple analog input device such as some joysticks can be connected directly to the motion controller. In the case of more sophisticated input devices, such as those that connect through a USB interface, a computer can serve as the interface between the input device and the motion controller 106.

Figure 3:
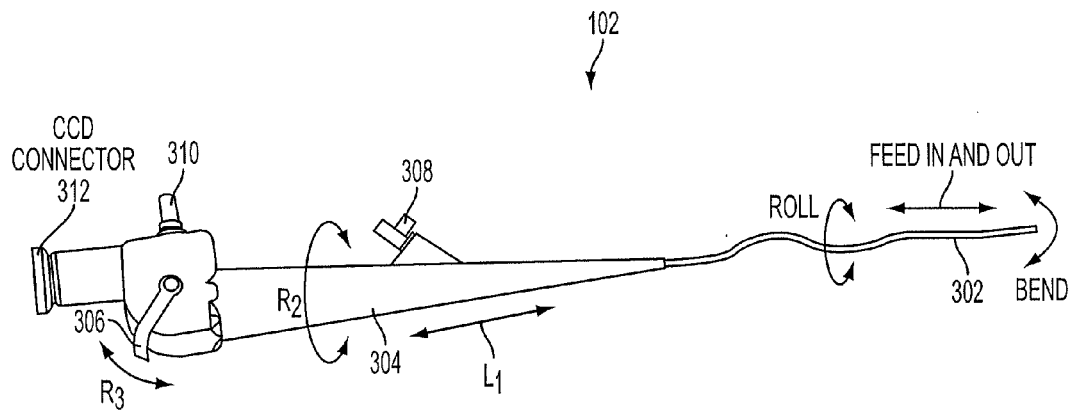
FIG. 3 is a schematic of the endoscope showing the key features.

FIG. 3 shows the key features of a typical endoscope 102, which can be described by its three degrees of freedom: L1 is the translation of the tip 302 in and out, R2 is the rotation of the body 304 (roll), and R3 is the rotation of the lever 306 that controls bending of the tip 302. The port 308 for insertion of tools, the light tunnel port 310, and the CCD connector 312 are also shown.

Figure 4:
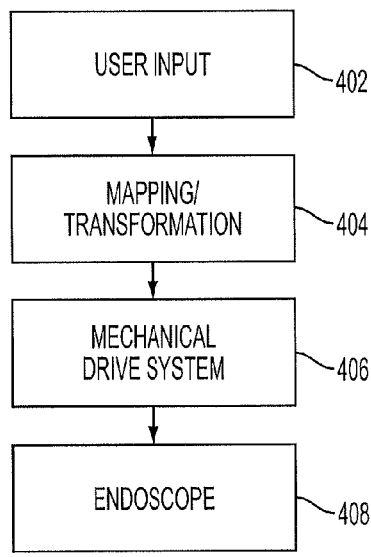
FIG. 4 is a block diagram showing the control scheme.

FIG. 4 shows the software control of the system. The user input is read in step 402 from the human/machine interface device which can be any input device with three or more degrees of freedom including a computer mouse, keyboard, SpaceNavigator mouse, gaming controller, or other suitable input device. The user input then undergoes a mathematical transformation in step 404 to put it in an appropriate format for the mechanical drive system, to which the transformed user input is supplied in step 406. The mechanical drive system then provides precision control of the endoscope in step 408.

Figure 5:
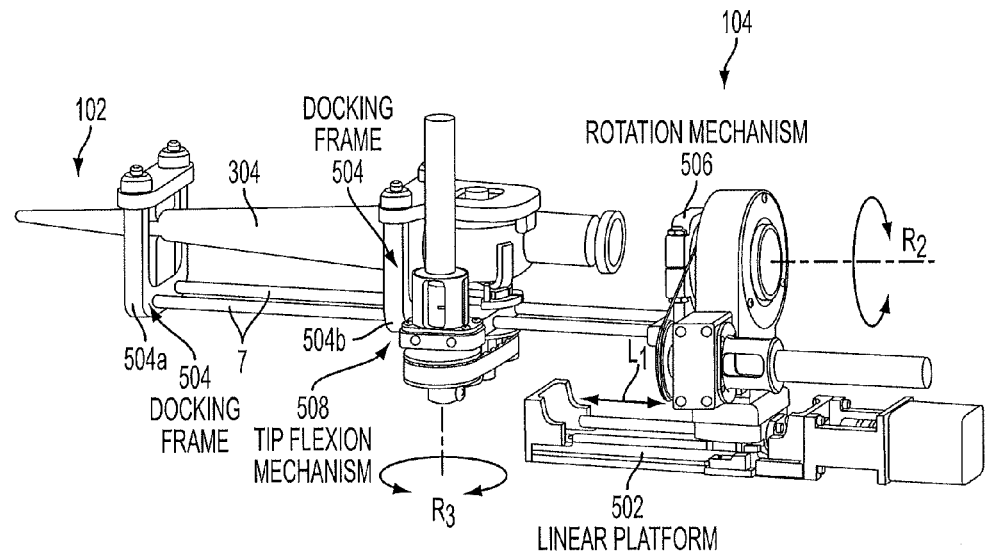
FIG. 5 is the electromechanical device in which the endoscope is placed.

The physical structure of the drive system 104 is shown in FIG. 5. The mechanical drive system provides three degrees of freedom: L1 for translation with the linear platform; R2 for roll with the rotation mechanism; and R3 for rotation of the lever 306 to effect bending of the tip of the endoscope. In the envisioned use, the endoscope 102 is placed on the mechanical drive system 104 after the flexible end is inserted to the region of interest within the patient, so the linear translation of the mechanical drive system 104 does not need to be large, and can be adequately covered by a linear platform 502. The body 304 of the scope 102 can be easily inserted into the docking frame 504, which is attached to the rotation mechanism 506 with two linear rods 7 that can be locked in place in the rotation mechanism 506 by means of set screws or other suitable locking mechanisms. The docking frame 504 includes a front or end docking frame 504a that is fixed at the end of the rods and an internal or adjustable docking frame 504b that holds the tip flexion mechanism 508. The position of the internal or adjustable docking frame 504b that includes the tip flexion mechanism 508 can be adjusted along the support rods 7 by means of set screws or other suitable locking mechanisms to accommodate scopes of varying size. The docking frame 504 includes a tip flexion mechanism 508, which, when actuated, provides control of the flexible tip 302 of the endoscope 102. The rotation mechanism 506 is connected to the top of the linear platform 502. When the rotation mechanism 506 is actuated, the scope handle and the tip flexion mechanism 508 rotate together, which provides a self-roll of the endoscope 102, shown as motion R2. When the linear platform 502 is actuated, the rotation mechanism 506 and the tip flexion mechanism 508 are driven, which provides the translation L1 of the endoscope. The motions L1, R2 and R3 of the endoscope 102 are thus actuated totally by the mechanical drive system 104.

Figure 6:
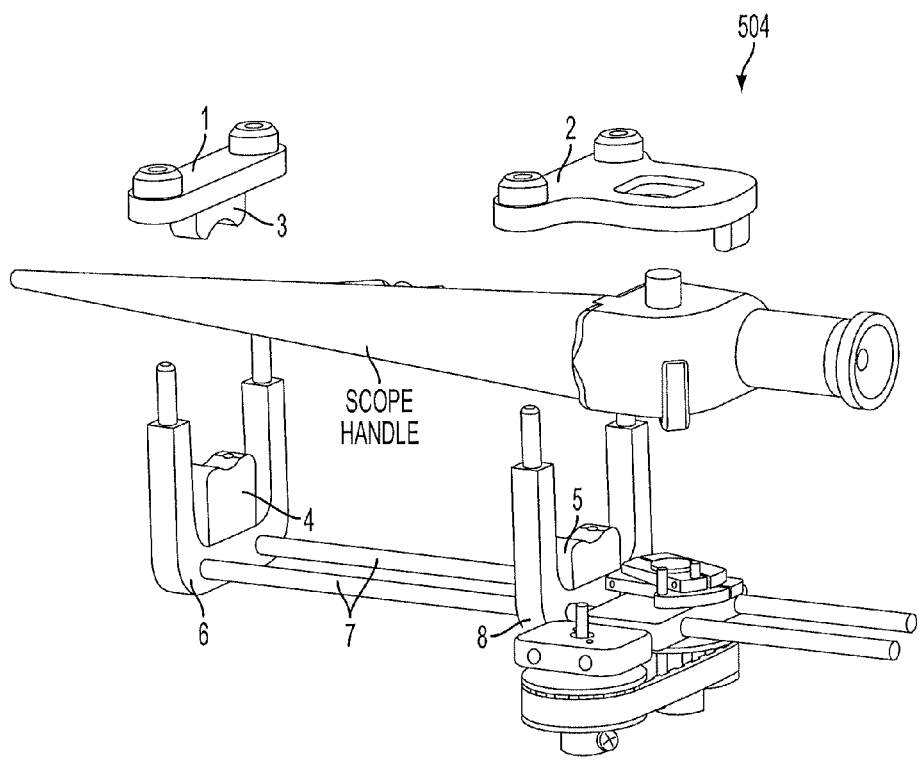
FIG. 6 illustrates how the endoscope can be easily inserted into the electromechanical device.

As shown in FIG. 6, the docking frame 504 includes U-shaped supports 6, 8 and support covers 1, 2 to firmly hold the endoscope handle and body. The U-shaped supports 6, 8 are connected to the support rods 7, which are attached to the rotation mechanism 506 of FIG. 5. The support covers 1, 2 can be quickly affixed to the U-shaped supports 6, 8 through quick connect nuts. The scope lower body adaptor 4 is incorporated within the U-shaped support 6, and together with the scope upper body adaptor 3 of the support cover 1, securely fixes the scope body in place. Similarly, shown on the right side, the lower body adaptor 5 within the U-shaped support 8, together with the specially designed support cover 2, securely fixes the other side of the scope body. Thus, the endoscope can be easily placed and removed into and out of the docking mechanism 504. This docking mechanism 504 can be specialized for each endoscope so that the invention can be generalized to the majority of flexible endoscopes in use today. This docking mechanism is a passive mechanical interface that serves to firmly hold the scope and connect it to the electromechanical frame. The docking mechanism can be sterilizable for multiple uses or designed as a single user device delivered in sterile packaging. Either the docking mechanism or the rest of the electromechanical box could be placed in a sterile bag during operating use to preserve a sterile field.

Figure 7:
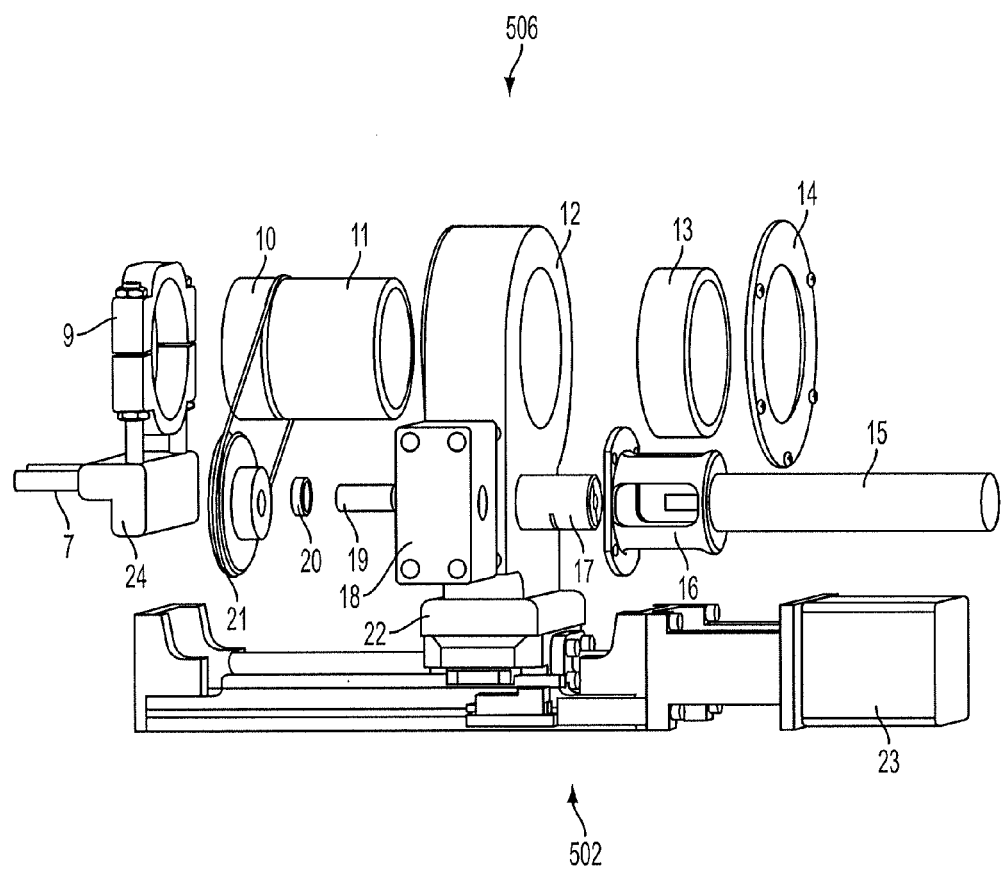
FIG. 7 is a detailed view showing the linear platform and roll motion.

FIG. 7 shows the structure of the rotational mechanism and linear platform. The base incorporates a motor 23 that drives the moving part 22, which achieves the linear motion L1 in FIG. 5. The bearing 13 is fixed by the cover 14 to the rotation frame 12, which is attached to the moving part 22. The rotation shaft 11 is seated in the rotation frame 12 with the bearing 13. The shaft adaptor 9 is fixed to the rotation shaft 11 with screws, while the docking adaptor 24 holds the support rods 7 and the support cover 9. The motor frame 16 is installed to the motor base 18, which is assembled to the rotation frame 12. The motor 15 is attached to the motor frame 16, the connector 17 links the motor 15 and the drive shaft 19, which is set in the motor frame 18 with a bearing 20. The drive wheel 21 is attached to the drive shaft 19 and translates the rotation from the motor 15 to the rotation shaft 11 with a closed flexible stainless cable loop 10. Thus when the motor 15 rotates the connector 17, the drive shaft 19, drive wheel 21, cable 10, rotation shaft 11, shaft adaptor 9, docking adaptor 24 and support rods 7 will all be rotated, which provides the rotation motion R2 in FIG. 5.

Figure 8:
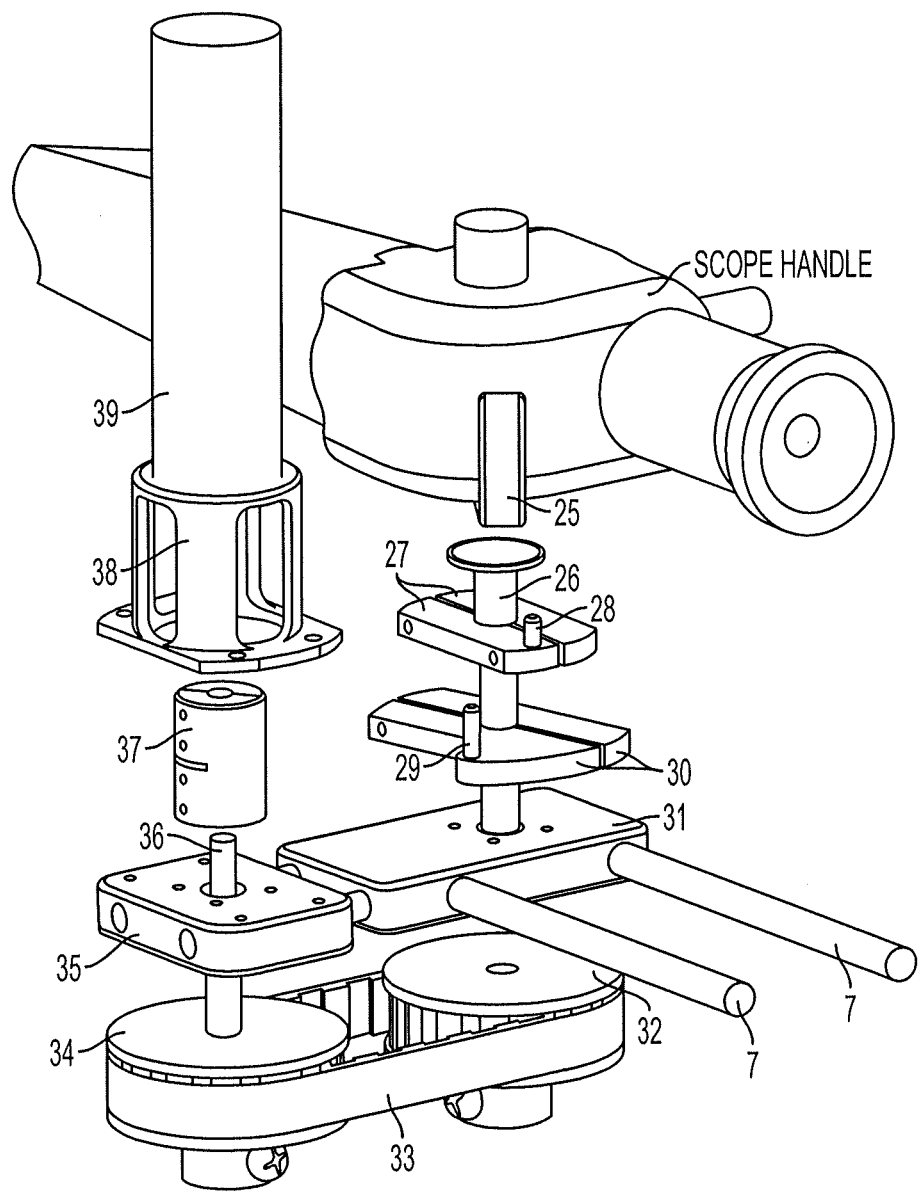
FIG. 8 is a detailed view showing the tip flexure mechanism.

FIG. 8 shows the structure for the tip flexion mechanism 508. As shown, the motor base 35 is assembled to the tip-flexion base 31 which supports the support rods 7 in FIG. 5. A tip-flexion shaft 26 is installed to the tip-flexion base 31 with bearings. Shaft graspers 27 and 30 are installed to the tip-flexion shaft 26 with screws. The position of poles 28, 29 on shaft graspers 27, 30 can be adjusted to fit and hold the lever 25 of the scope handle. The tip-flexion shaft 26 is attached to the pulley 32, which is connected to pulley 34 by a belt 33. The pulley 34 is attached to the drive shaft 36, which is installed to the motor base 35 with bearings. The tip-flexion motor 39 is connected to the motor base 35 with a motor frame 38. A connector 37 links the tip-flexion motor 39 shaft to the drive shaft 36. Thus when the tip-flexion motor 39 rotates, the connector 37, the drive shaft 36, the pulley 34, the belt 33, the pulley 32, the tip-flexion shaft 26, the shaft grasper 27, 30 and the poles 28, 29 all rotate, and the lever 25 of the scope will be rotated, which is R3 in FIG. 5. While it is contemplated to use a cable for actuating the rotation and belt actuating the flexion, another suitable mechanical linkage such as a belt or gears can do the same.

Figure 9:
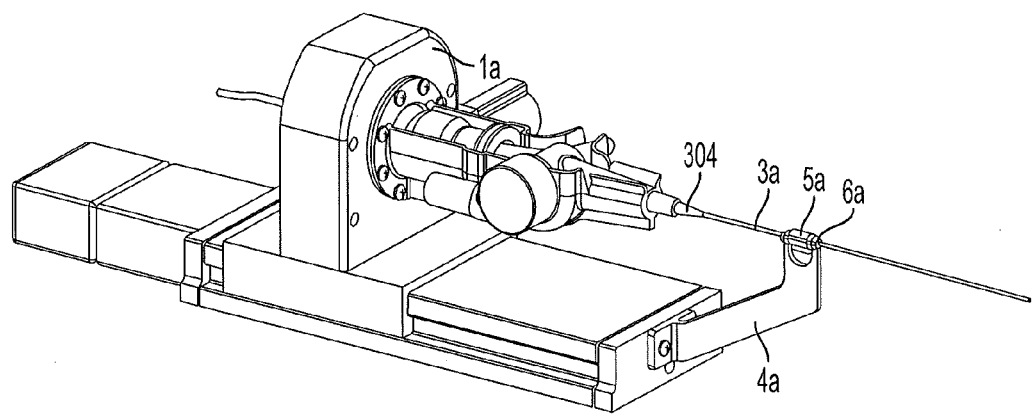
FIG. 9 is a detailed view of a guide for the endoscope shaft.

FIG. 9 shows a guide that might be used in conjunction with the mechanical drive box and could reduce the tendency for buckling of the flexible shaft 3a of the endoscope to occur. There will be an unsupported span of flexible shaft 3a between the point at which the flexible shaft emerges from the endoscope body 304 and the point at which the flexible shaft enters the patient. As a minimum, the length of this unsupported span must be equal to the distance by which the endoscope will be advanced after it has been placed in the patient and is ready to be inserted into the mechanical drive system. However, as a practical matter, the length of the flexible shaft will be chosen from one of a limited set of available lengths, based on patient anatomy/size and the procedure to be performed, and, therefore, the unsupported span will be equal to the length of the flexible shaft chosen minus the distance to which the flexible shaft has been manually advanced prior to insertion into the mechanical drive assembly. Since the unsupported span length is not known a priori to a high degree of accuracy, nor precisely what the advancement force will be, it is desirable to have provision for placement of a guide 5a at a point that is halfway or thereabouts along the unsupported span of the flexible shaft 3a. The position of the flexible shaft guide 5a will be adjustable to allow the practitioner to position it at or near the halfway point of the unsupported span that arises. A swivel lock 6a rotates out of the way so that the flexible shaft 3a can mount into the guide 5a, then swivels back to into position to capture the flexible shaft. The catheter is free to translate and rotate inside the guide. The effect of the guide 5a is to reduce the length of the unsupported span by half, and, hence, increase the advancement force at which buckling occurs. The guide 5a could be easily moved out of the way, if, during advancement, it impedes further advancement. At this point, the unsupported span is shorter by a factor of two, and it is no longer needed. If the guide 5a of FIG. 9 were to prove inadequate to prevent buckling in certain endoscopic applications, alternative means could be employed that would maintain tension in the unsupported span of the flexible shaft. For example, a pair of opposing rollers that gently pinch the flexible shaft (as it runs between them) would be placed close to the patient entry point. Pre-wound rotary springs would allow the rollers to maintain tension in the flexible shaft over the span between the rollers and the emergence of the flexible shaft from the endoscope, thereby preventing buckling.

For mechanical safety, the preferred embodiment uses limit switches on each axis to prevent any problems with "runaway" of the controller. However, in the alternative, a slip clutch or torque limiter could be used on each axis to improve safety.

While a preferred embodiment and variations thereof have been set forth above, those skilled in the art who have reviewed the present disclosure will readily appreciate that other embodiments can be realized within the scope of the invention. For example, while the invention has particular relevance to ureteroscopy, it can be used for any type of endoscopy. Also, it can be used with human or animal patients. Therefore, the present invention should be construed as limited only by the appended claims.

We claim:

1. A motorized system for improving manipulation of an endoscope, comprising:
 a mechanical device that holds and drives the endoscope;
 a motion control system having processing circuitry configured to control the mechanical device; and
 a human/machine interface that allows a user to control the mechanical device through the motion control system;
 wherein the mechanical device comprises:
 a base;
 a linear platform that causes linear movement of the endoscope, the linear platform being mounted on the base and being linearly movable relative to the base;
 a rotation mechanism that causes rotation of the endoscope and of a support that includes two parallel support rods, the rotation mechanism being mounted on the linear platform and being movable with the linear platform; and
 a tip-flexion mechanism including a motor that provides motive power that causes bending of the tip of the endoscope, the tip-flexion mechanism being mounted on the support and being movable with the linear platform, wherein
 the rotation mechanism further rotates the tip-flexion mechanism together with rotation of the endoscope, and wherein
 the two parallel support rods pass through a frame that holds the tip-flexion mechanism, and the frame that holds the tip-flexion mechanism is adjustable along a length of the two parallel support rods.

2. The motorized system of claim 1, wherein the human/machine interface comprises a six-degree-of-freedom (6-DOF) controller.

3. The motorized system of claim 2, wherein the 6-DOF controller comprises a mouse.

4. The motorized system of claim 1, wherein the linear platform comprises:
 a moving part mounted on the base being linearly movable relative to the base; and
 the two parallel support rods, extending from the moving part, on which the rotation mechanism and the tip-flexion mechanism are mounted.

5. The motorized system of claim 1, wherein the linear platform further comprises at least one member for removably holding a body of the endoscope.

6. The motorized system of claim 5, comprising at least one said member for removably holding the body of the endoscope, and
 wherein said at least one member for removably holding the body of the endoscope comprises:
 a docking frame for holding the handle of the endoscope; and
 a cover panel removably attachable to the docking frame for retaining the body of the endoscope.

7. The motorized system of claim 6, wherein the tip-flexion mechanism is attached to the docking frame.

8. The motorized system of claim 6, wherein the rotation mechanism comprises:
 a rotation shaft for engaging with the handle of the endoscope;
 a motor;
 a drive wheel coaxial with the motor; and
 a loop for conveying rotational movement from the drive wheel to the rotation shaft.

9. The motorized system of claim 1, wherein the tip-flexion mechanism is adapted to engage with a lever on a handle of the endoscope to actuate the lever to bend the tip of the endoscope.

10. The motorized system of claim 9, wherein the tip-flexion mechanism comprises:
 an engaging element for engaging with the lever; and
 a mechanical linkage for conveying movement from the motor to the engaging element.

11. The motorized system of claim 10, wherein the mechanical linkage comprises:
 a first belt pulley connected coaxially to the motor;
 a belt;
 a second belt pulley connected to the first belt pulley by the belt; and
 a shaft connected coaxially to the second pulley; and
 wherein the engaging element is on the shaft.

12. The motorized system of claim 10, wherein the engaging element comprises a pole.

13. The motorized system of claim 1, wherein the motion control system comprises a computer programmed to provide automatic or semi-automatic control of the mechanical device.

14. A method for using and manipulating an endoscope, the method comprising:
(a) providing a motorized system for improving manipulation of an endoscope, the motorized system comprising:
a mechanical device that holds and drive the endoscope,
a motion control system having processing circuitry configured to control the mechanical device, and
a human/machine interface that allows a user to control the mechanical device through the motion control system,
wherein the mechanical device comprises:
a base,
a linear platform that causes linear movement of the endoscope, the linear platform being mounted on the base and being linearly movable relative to the base,
a rotation mechanism that causes rotation of the endoscope and of a support that includes two parallel support rods, the rotation mechanism being mounted on the linear platform and being movable with the linear platform, and
a tip-flexion mechanism including a motor that provides motive power that causes bending of the tip of the endoscope, the tip-flexion mechanism being mounted on the support and being movable with the linear platform, wherein
the rotation mechanism further rotates the tip-flexion mechanism together with rotation of the endoscope, and wherein
the two parallel support rods pass through a frame that holds the tip-flexion mechanism, and the frame that holds the tip-flexion mechanism is adjustable along a length of the two parallel support rods;
(b) providing the endoscope in the device;
(c) inserting the endoscope into a patient; and
(d) using the motorized system to manipulate the endoscope within the patient.

15. The method of claim 14, wherein the human/machine interface comprises a six-degree-of-freedom (6-DOF) controller.

16. The method of claim 15, wherein the 6-DOF controller comprises a mouse.

17. The method of claim 14, wherein the linear platform comprises:
a moving part mounted on the base being linearly movable relative to the base; and
the two parallel support rods, extending from the moving part, on which the rotation mechanism and the tip-flexion mechanism are mounted.

18. The method of claim 14, wherein the linear platform further comprises at least one member for removably holding a body of the endoscope, and wherein step (b) comprises inserting the endoscope into the at least one member.

19. The method of claim 18, wherein the at least one member for removably holding the body of the endoscope comprises:
a docking frame for holding the body of the endoscope; and
a cover panel removably attachable to the body frame for retaining the body of the endoscope.

20. The method of claim 19, wherein the tip-flexion mechanism is attached to the docking frame.

21. The method of claim 19, wherein the rotation mechanism comprises:
a rotation shaft for engaging with the handle of the endoscope;
a motor;
a drive wheel coaxial with the motor; and
a loop for conveying rotational movement from the drive wheel to the rotation shaft.

22. The method of claim 14, wherein the tip-flexion mechanism is adapted to engage with a lever on a handle of the endoscope to actuate the lever to bend the tip of the endoscope.

23. The method of claim 22, wherein the tip-flexion mechanism comprises:
an engaging element for engaging with the lever; and
a mechanical linkage for conveying movement from the motor to the engaging element.

24. The method of claim 23, wherein the mechanical linkage comprises:
a first belt pulley connected coaxially to the motor;
a belt;
a second belt pulley connected to the first belt pulley by the belt; and
a shaft connected coaxially to the second pulley; and
wherein the engaging element is on the shaft.

25. The method of claim 23, wherein the engaging element comprises a pole.

26. The method of claim 14, wherein the motion control system comprises a computer programmed to provide automatic or semi-automatic control of the mechanical device, and
wherein step (d) is performed under the automatic or semi-automatic control of the computer.

27. The method of claim 14, wherein the endoscope is an ureteroscope.

28. The method of claim 14, wherein step (c) comprises manually inserting the endoscope into a region of interest in the patient and using the mechanical device to move the endoscope within the region of interest.

29. A motorized system for improving manipulation of an endoscope, comprising:
a mechanical device that holds and drives the endoscope;
a motion control system having processing circuitry configured to control the mechanical device; and
a human/machine interface that allows a user to control the mechanical device through the motion control system;
wherein the mechanical device comprises:
a base;
a linear platform and a first motor that causes linear movement of the endoscope, the linear platform being mounted on the base and being linearly movable by the first motor relative to the base;
a rotation mechanism including a second motor that rotates a support that includes two parallel support rods to cause a rotation of the endoscope in a first rotation direction, the rotation mechanism being mounted on the linear platform and being linearly movable with the linear platform by the first motor; and
a tip-flexion mechanism including a third motor that provides motive power that causes bending of a tip of the endoscope in a second rotation direction that is different from the first rotation direction, the tip-flexion mechanism being mounted on the support and being rotatable in the first rotation direction by the second motor and being linearly movable with the linear platform by the first motor, wherein the rotation mechanism rotates the tip-flexion mechanism together with rotation of the endoscope in the first rotation direction, and wherein the two parallel support rods pass through a frame that holds the tip-flexion mechanism, and the frame that holds the tip-flexion mechanism is adjustable along a length of the two parallel support rods.

30. The motorized system of claim 29, wherein the frame that holds the tip-flexion mechanism includes a first U-shaped support and a first removable cover that hold a first side of a body of the endoscope.

31. The motorized system of claim 30, wherein a second U-shaped support and a second removable cover hold a second side of the body of the endoscope that is closer to the tip of the endoscope than the first side, and the second U-shaped support is fixed to ends of the two parallel support rods.

* * * * *